(12) United States Patent
Papp et al.

(10) Patent No.: US 10,945,887 B2
(45) Date of Patent: Mar. 16, 2021

(54) METHOD AND SYSTEM FOR AN ACCELERATED REACTION OF DARKENING OF THE OPTICAL DEVICE IN PERSONAL PROTECTIVE EQUIPMENT

(71) Applicant: TRAFIMET GROUP S.P.A, Castegnero (IT)

(72) Inventors: Robert Papp, Dlha nad Vahom (SK); Kristian Liptak, Velke Ulany (SK); Ing. Robert Lauko, Bratislava-Stare Mesto (SK)

(73) Assignee: Trafimet Group S.P.A., Castegnero (IT)

( * ) Notice: Subject to any disclaimer, the term of this patent is extended or adjusted under 35 U.S.C. 154(b) by 186 days.

(21) Appl. No.: 15/779,082

(22) PCT Filed: May 31, 2016

(86) PCT No.: PCT/IB2016/053188
§ 371 (c)(1),
(2) Date: May 24, 2018

(87) PCT Pub. No.: WO2017/098340
PCT Pub. Date: Jun. 15, 2017

(65) Prior Publication Data
US 2018/0353330 A1   Dec. 13, 2018

(30) Foreign Application Priority Data

Dec. 7, 2015 (SK) .............................. 50116-2015 U
May 30, 2016 (SK) ................................. 50031-2016
May 30, 2016 (SK) .............................. 50071-2016 U (51) Int. Cl.
*B23K 9/32* (2006.01)
*A61F 9/06* (2006.01)
(Continued)

(52) U.S. Cl.
CPC .......... *A61F 9/067* (2013.01); *A41D 13/1184* (2013.01); *A61F 9/06* (2013.01);
(Continued)

(58) Field of Classification Search
CPC .. B23K 9/10; B23K 9/32; B23K 9/322; A61F 9/067; A61F 9/06; A61F 9/04; A61F 9/065; G02F 1/13; G02F 1/133
See application file for complete search history.

(56) References Cited

U.S. PATENT DOCUMENTS 4,638,146 A * 1/1987 Koyama ............... G02F 1/0556
219/132
5,477,091 A   12/1995 Fiorina et al.
(Continued)

FOREIGN PATENT DOCUMENTS

CN        101247917 A     8/2008
DE     102006056360 A1    7/2007
(Continued)

OTHER PUBLICATIONS

Search report in corresponding CN 2016800715321 dated Jun. 7, 2018 (pp. 1-2).
(Continued)

*Primary Examiner* — Brian W Jennison
(74) *Attorney, Agent, or Firm* — Millen, White, Zelano & Branigan, P.C.; William Nixon (57) ABSTRACT

System has an optical sensor (1), an aperture with the optical element (2) with the changeable permeability and an activation light (3) emitting radiation, which is detected by the optical sensor (1). The activation light is connected with the switch (4) and it is placed within the reach of the optical sensor (1). Within a device which realizes the technological process with the luminous manifestation the instruction for the beginning of a given technological process is detected
(Continued)

and on the basis of this instruction the activation light (3) lights up. This activates the optical sensor (1) by means of the activation light (3) before the optical sensor (1) detects the luminous manifestation of the technological process itself. The activation light (3) can be a simple infrared LED diode. The advantage lies in the fact that the protective device itself does not have to be modified in any way and its reaction time can be shortened to zero, or negative reaction time can be achieved since we use time passing during the initiation of the technological process before the appearance of the luminous manifestation for the darkening.

22 Claims, 9 Drawing Sheets (51) Int. Cl.
B23K 9/173 (2006.01)
A41D 13/11 (2006.01)
G02C 7/10 (2006.01)

(52) U.S. Cl.
CPC .............. B23K 9/173 (2013.01); B23K 9/322 (2013.01); G02C 7/10 (2013.01); *A41D 2600/202* (2013.01)

(56) References Cited

U.S. PATENT DOCUMENTS

| | | | |
|---|---|---|---|
| 5,880,793 A | 3/1999 | Gunz et al. | |
| 5,975,695 A | 11/1999 | Baiocchi et al. | |
| 6,483,090 B1 | 11/2002 | Bae | |
| 6,734,393 B1 | 5/2004 | Friedl et al. | |
| 7,470,880 B2 | 12/2008 | Huh | |
| 2010/0089887 A1 | 4/2010 | Friedl et al. | |
| 2010/0090997 A1 | 4/2010 | Huh | |
| 2011/0109232 A1* | 5/2011 | Schulz | G01J 1/02 315/151 |
| 2013/0128135 A1 | 5/2013 | Sundell | |
| 2014/0021337 A1 | 1/2014 | Huh | |
| 2018/0353330 A1 | 12/2018 | Papp et al. | |

FOREIGN PATENT DOCUMENTS

| | | |
|---|---|---|
| EP | 0550348 B1 | 2/1997 |
| EP | 0579076 B1 | 9/1997 |
| FR | 2787700 A1 | 6/2000 |
| JP | 10272151 A | 10/1998 |
| JP | 2010094708 A | 4/2010 |
| SK | 501162015 U1 | 7/2016 |

OTHER PUBLICATIONS

Search report in corresponding EP 3178454 dated Oct. 19, 2016 (pp. 1-14).

Search report in corresponding PCT/IB2016/053188 dated Oct. 19, 2016 (pp. 1-16).

Search report in corresponding SK 50031-2016 dated Apr. 12, 2017 (p. 1).

\* cited by examiner

METHOD AND SYSTEM FOR AN ACCELERATED REACTION OF DARKENING OF THE OPTICAL DEVICE IN PERSONAL PROTECTIVE EQUIPMENT

FIELD OF TECHNOLOGY

The invention concerns the shortening of the reaction time of the auto-darkening optical device in personal protective equipment, such as welding helmets, where the optical device darkens in reaction to an intensive light emission accompanying the running technological process, for example in reaction to the ignited electric arc during the process of welding, cutting, etc.

PRIOR ART

Personal protective equipment, such as auto-darkening goggles, shields, masks, helmets, etc., are used in order to protect the sight during the process of welding, cutting and similar processes accompanied by an intensive light emission. The essential part of such protective equipment is an optical device capable of changing its light permeability following a signal from the control circuit (Auto-Darkening Filters, ADF). The electric arc emits intensive ultraviolet, infrared and visible light radiation. The light sensitive sensor issues an instruction to dim or darken the optical device and the darkened optical device prevents transmission of the harmful radiation to the eyes.

Figure 1:
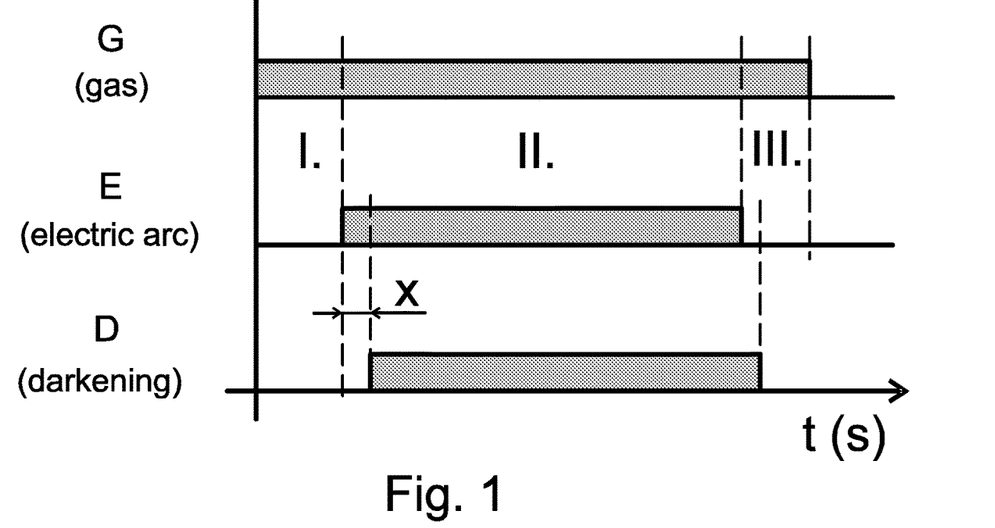
FIG. 1 depicts a time graph with the course of the welding and darkening of the welding helmet pursuant to the state of the art. The process G corresponds to the inflow of the protective gas and it begins with the pressing of the trigger on the welding gun. The process E is an ignition and burning of the electric arc. The process D is the darkening of the welding helmet. The time period x denotes a delay of the darkening of the protective equipment in relation to the light emission.
Figure 2:
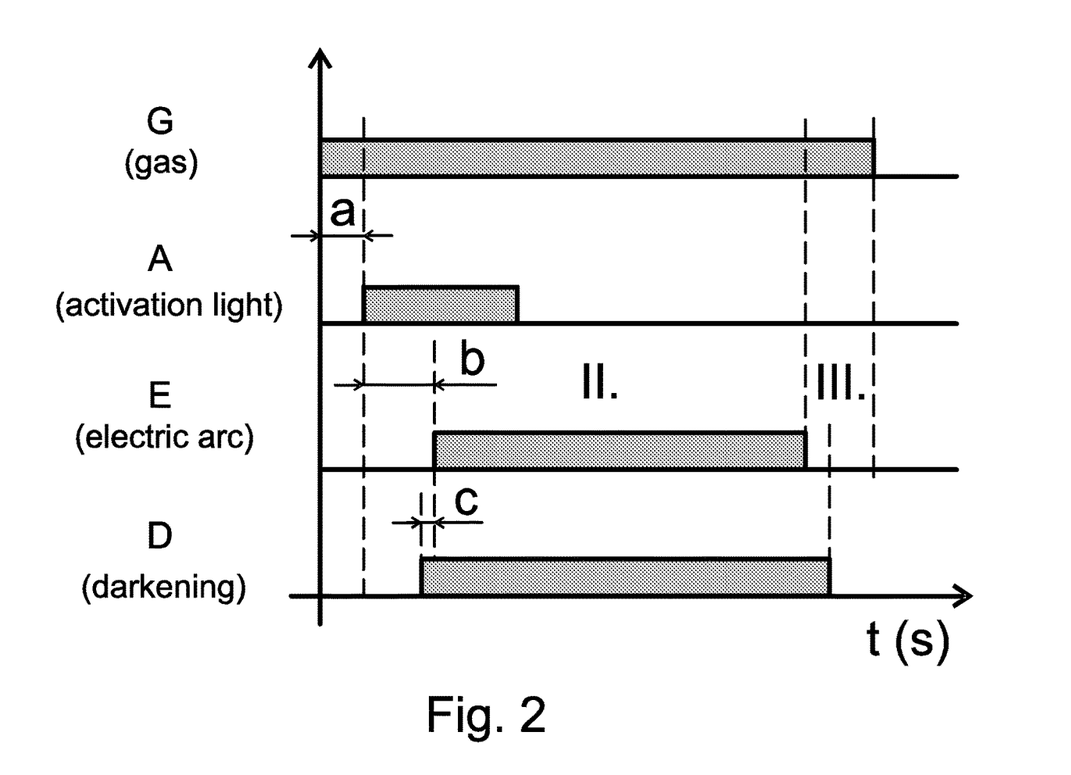
FIG. 2 is a time graph with the course of the welding and darkening of the welding helmet. The process A depicts the lighting of the activation light. The phase I in FIGS. 1 and 2 is a pre-gas phase, the phase II is a period of the burning electric arc, the phase III in FIGS. 1 and 2 is a post-gas phase. The time a is an intentional delay of the turning on of the activation light with regard to the instruction to start the technological process. The time b is the advance time of the activation light before the light emission. The time c is the advance time of the darkening before the generation of the light emission.
Figure 3:
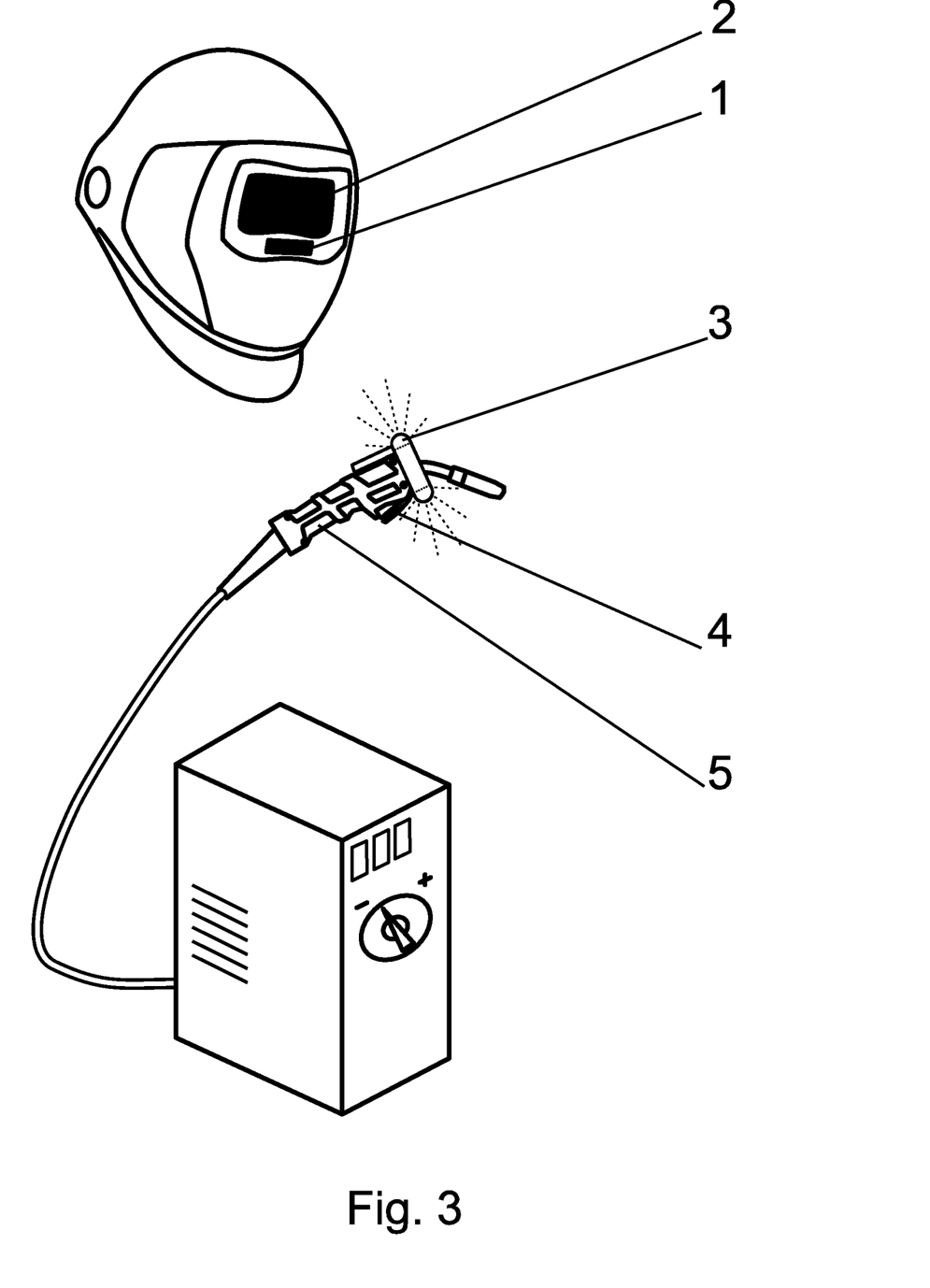
FIG. 3 is an axonometric view of the welding workplace with a manually controlled welding gun on which a ring-shaped activation light is placed. The interrupted lines stemming from the activation light depict the infrared radiation.
Figure 4:
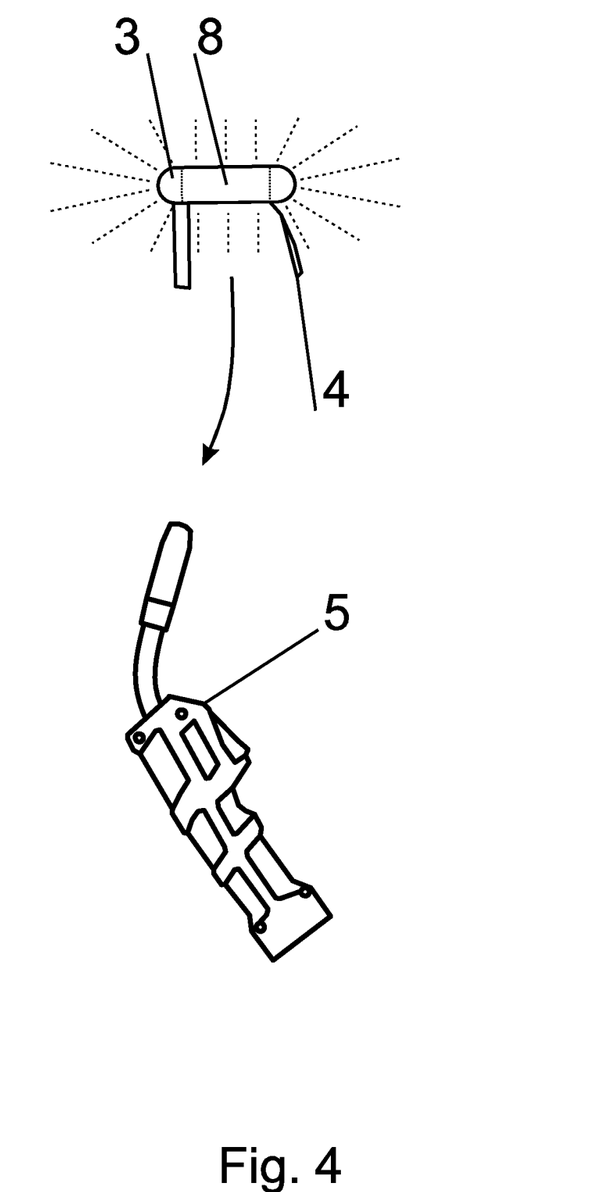
FIG. 4 depicts the activation light. The arrow denotes the direction in which the ring with the activation light is put on the welding gun. The interrupted lines stemming from the activation light depict the infrared radiation which is propagating the activation light.
Figure 5:
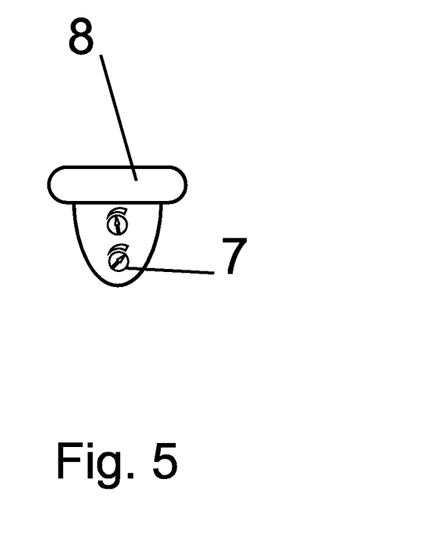
FIG. 5 shows the activation light from FIG. 4 rotated in such a way that it is possible to see its body with the control elements.
Figure 9:
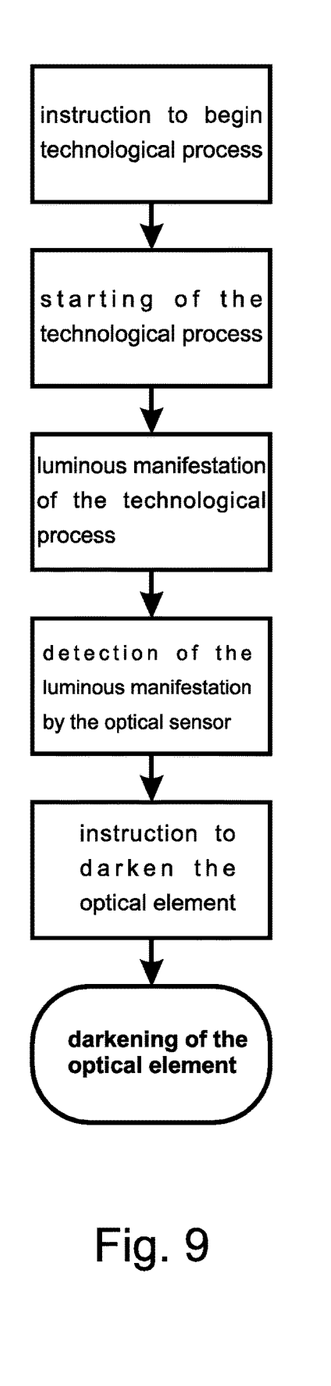
FIG. 9 is an algorithm of the procedure followed during the darkening of the welding helmet pursuant to the state of the art.
Figure 10:
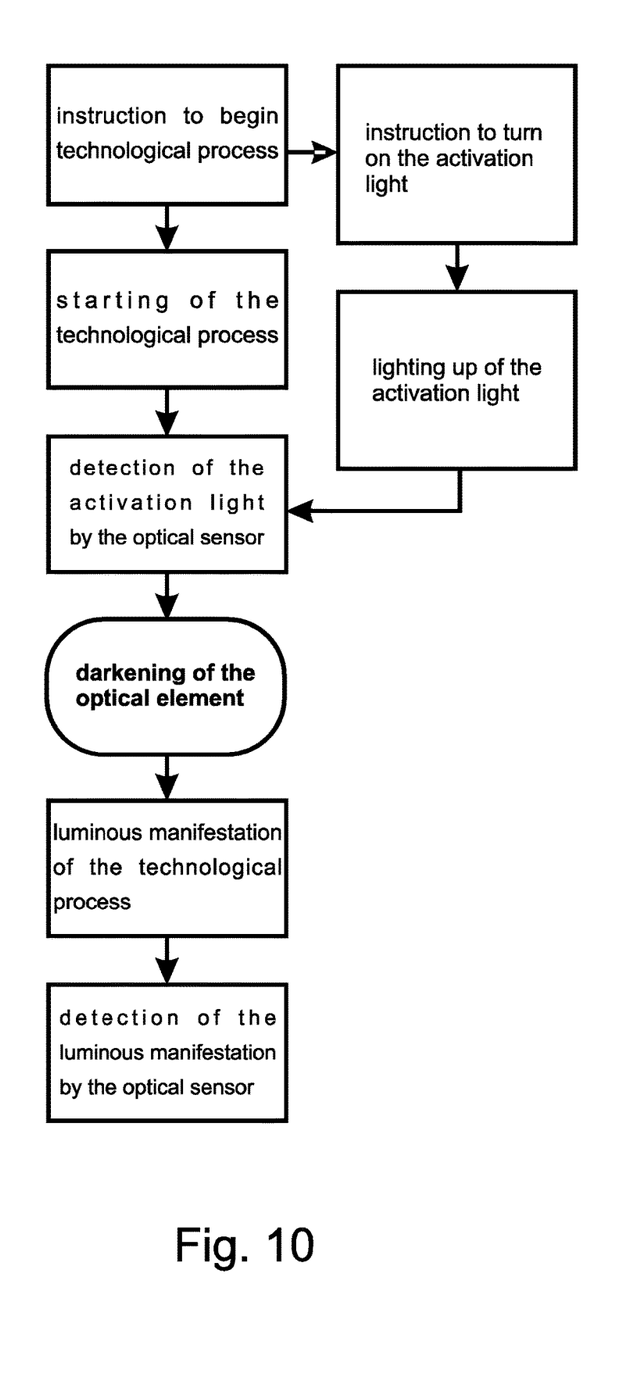
FIG. 10 is a procedure followed during the darkening of the protective equipment with the use of the activation light.
Figure 11:
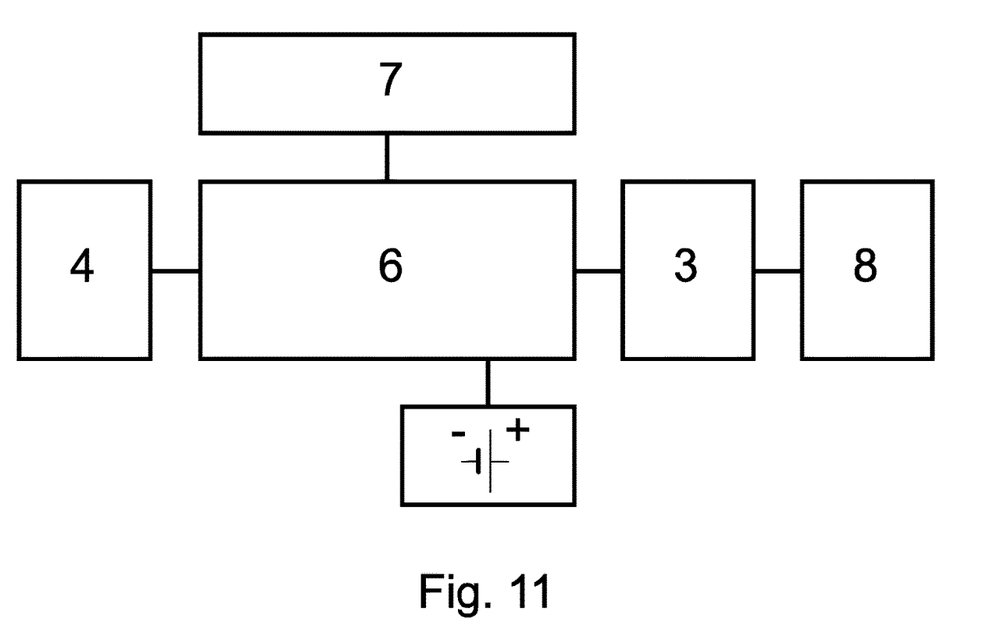
FIG. 11 is a block diagram of the basic elements of the control of the activation light.

In order to achieve reliable sight protection, the darkening of the optical device must be triggered as soon as the dangerous light phenomenon is detected, for example after the ignition of the electric arc during the welding process. There are multiple solutions that can be used to fulfill this technical task, for instance solutions described in the publications WO2005009309A1, WO2011097841A1, U.S. Pat. No. 8,264,265B2, US2013128135A1, which aim at shortening the time of the detection of the dangerous light emission and at shortening the reaction time of the optical device itself; i.e., they shorten the time needed by the optical device to achieve the optical change. The duration of these two stages of detection and reaction is inferior to 0.3 ms; certain quality welding helmets are able to darken within 0.05 ms (1/20 000 s) after the ignition of the electric arc (FIGS. 1 and 9). In absolute terms these time lapses are short and it is problematic to shorten them even further. However, in order to increase the sight protection, it would be preferable to achieve a zero reaction time.

Publications US2003206491A1 and WO2008082751A1 describe the functioning of a voice-controlled welding helmet; welder can darken the optical device in advance by a voice command. Other solutions, based on a similar principle, include a control button or similar element allowing darkening even before the electric arc is ignited. Such solutions are, however, uncomfortable since they require continuous issuing of commands which is contrary to the requirement of the automated operation.

An improvement is offered in the U.S. Pat. No. 7,812,279 B2 where, during welding in a protective atmosphere, the welding helmet is controlled by a command from the welding apparatus. In this kind of welding, the electric arc is ignited with a certain delay after the activation of the welding gun trigger. This delay is in fractions of a second and is caused intentionally in order to allow supply of the protective gas from the pressure vessel to the welding environment. This allows to issue a command to darken the welding helmet before the ignition of the electric arc. In case of U.S. Pat. No. 7,812,279 B2, the command to darken is transmitted to the helmet via the radio transmission. However, this is possible only if the helmet contains a receiving device for the communication with the welding apparatus. This solution therefore cannot be used with the existing auto-darkening helmets. The use of the radio transmission between transmitter and receiver on the helmet is problematic; there is a strong electromagnetic field during welding that can hamper the correct transmission. The complications arise at the working places where multiple welding processes take place simultaneously due to the interference of multiple radio frequency communication channels. A drawback also lies in the high energy demand as well as in the overall complexity of the receiving circuit that requires a relatively powerful independent source of energy for a proper functioning.

It is necessary to come up with such a solution, that does not exist so far, which would have low energy demands, which could be used with all sorts of protective equipment, which would shorten the time between the creation of the light phenomenon and the darkening of the optical device, and which would be comfortable for personnel to wear and easy to operate.

A protective device in accordance with the prior art is known from document U.S. Pat. No. 4,638,146 A.

ESSENCE OF THE INVENTION

The abovementioned deficiencies are significantly remedied by a system and a method according to the independent claims.

In particular, an exemplary method relates to an accelerated reaction of darkening of the optical device in personal protective equipment for the sight protection, where an optical sensor on the protective equipment detects the light emission accompanying the technological process and following the signal from the optical sensor the darkening of the optical device is activated. Thus, the darkening limits the penetration of the radiation from the light emission to the eyes. The device running the technological process with the light emission detects an instruction (command) to begin such technological process and subsequently, following this instruction, an activation light is turned on directing the light beam towards the optical sensor on the protective equipment in order to activate the optical sensor by means of the activation light even before the optical sensor detects the light emission from the technological process itself. By activation of the optical sensor is meant the detection of the light by the optical sensor resulting in the issuing of the instruction or command to darken the optical device.

In simple terms, the existing processing cycle of the automatic darkening of the optical device used hitherto is as follows:

1. instruction to begin a technological process;
2. starting of the technological process;
3. light emission from the technological process;
4. detection of the light emission by the optical sensor;
5. instruction to darken the optical device;
6. darkening of the optical device.

We can see that in the first three steps of the prior state of the art the protective equipment is only in the standby mode, it does not effectuate any activity. With the solution of this invention, the control of the protective equipment begins in the very first step, which guarantees crucial time needed for the darkening:
1. instruction to begin a technological process+instruction to turn on the activation light;
2. starting of the technological process+lighting up of the activation light;
3. detection of the activation light by the optical sensor;
4. light emission from the technological process+darkening of the optical device;
5. detection of the light emission by the optical sensor; the optical device remains darkened.

It is sufficient if the activation light is turned on until the optical device of the protective equipment detects the light emission from the technological process itself. The activation light will usually temporarily overlap with the detection of the light emission, after which the activation light will be turned off in order to lower the overall energy demands. Should the activation light remain on for an unnecessarily long time, it could cause darkening of the optical device at the time when the technological process itself along with the light emission is already completed. In any case, the activation light should be on at least during the period of time corresponding to the pre-ignition time of the activation light before the light emission from the technological process is detected. The value of the temporal overlap of the light beam of the activation light with the light emission can be adjusted by a control element. Generally, the overall duration of the activation light will not be longer than 2 to 5 s.

In order to better coordinate the duration of the activation light with the running technological process, it will be preferable to apply a set-up where the control mechanism of the activation light is capable of recognizing the creation of the light emission, i.e. for example directly through its own second optical sensor or indirectly through the change in the electric current in the electric arc, etc. This recognition is not necessary for the functioning of the activation light; the activation light can be simply turned off after, say, one second from the lighting up. But there are working operations (e.g. short spot or line welds) where a long period of the activation light would, actually, overlap with the ending of the given phase of the technological process. In such case the optical device would be darkened despite the ending of the light emission. If the control mechanism of the activation light can recognize the beginning of the light emission, the activation light can be turned off instantly because the darkening of the optical device will be secured on the basis of the sensing of the light emission.

Recognition of the light emission for the purpose of turning off the activation light can be guaranteed by the second optical sensor placed, for example, in the vicinity of the activation light nearby the body of the welding gun. The term "welding gun" designates a welding torch used for welding, i.e. it mainly defines the place of welding. The optical sensor necessary for the recognition of the light emission is described as "second" only for the sake of distinguishing it from the indispensable optical sensor on the protective equipment itself. In the framework of this invention but in another arrangement, the instruction to turn off the activation light after the creation of the light emission can arise from the current-measurement instrument in the supply cables of the welding gun, or such instruction can be part of the control mechanism of the automated welding workplace. The shortening of the activation light duration lowers energy demands and increases the longevity of the used battery or accumulator.

Time lapse between the instruction to begin the technological process and its light emission can differ depending on the particular type of the technological process. In case of welding with non-melting electrode under an inert gas protective atmosphere (TIG, WIG), or welding with wire electrode (MIG-MAG) in a protective atmosphere of CO2 or CO2 with argon (Metal Inert Gas, Metal Active Gas), the electric arc is intentionally ignited with a delay after the welding gun trigger is pressed. This delay (pre-gas time) can be so long that an immediate lighting up of the activation light would result in too early darkening, which can be uncomfortable or confusing for the welder. The proposed solution can basically achieve a negative reaction time of the darkening in response to the light emission. Therefore, it is preferable if the command to initiate the activation light is delayed after the command to initiate the technological process. It will be possible to adjust this delay according to a preferred set-up, usually up to 2 seconds.

In order to achieve a balance between a reliable sight protection and the comfort of the welder, it is preferable to achieve certain, very short negative reaction time between the light emission and the darkening of the optical equipment. It is problematic to achieve a zero reaction time that would be technically stable; a setting with the positive reaction time results in an inadequate use of the potential of this invention. In order to optimize the short negative reaction time, it is possible to apply a setting where the control of the activation light involves recognition of the light emission of the technological process. Such recognition can also serve to turn off the activation light after the creation of the light emission as stated in the description above. The control of the activation light can include an adaptation algorithm that will allow the control mechanism to learn to set the optimal value of the delay in relation to the moment of the instruction to initiate the technological process. The adaptation can begin, for example, by setting the delay to zero at the first turning on of the activation light and at the same time, by measuring the time lapse until the light emission is recorded. This time period, decreased by a small pre-ignition value, will be used for correcting the subsequent delay. The control mechanism of the activation light will continually learn how long is the time period, including its statistical margin of error, between the instruction to begin the technological process and its light emission. After certain period of inactivity which could indicate a transition to another workplace or the period of time following the reset, the adaptation mechanism starts anew. Moreover, it is possible to adjust the delay manually in combination with the automatic adjustment based on the measurement of time.

If the system includes also a second optical sensor, i.e. a sensor of the light emission itself, the method can include a learning algorithm which analyzes the time between the pressing of the trigger of the technological process and its light emission. After the time is measured, at the next pressing of the trigger an emitting signal of the activation light is sent just before the light emission, which saves the energy of the power supply of the activation light. The control process of the activation light can be programmed as "multi-stroke"— for example, two- or four-stroke welding where the welding machine reacts to one pressing of the trigger by igniting the electric arc while keeping it functioning until the second pressing of the trigger. The electric arc will be switched off after this second pressing of the trigger. It is possible to proceed in the same way in the pulse regime where, after the first pressing of the trigger, the welding machine initiates the pulse welding with the discontinuous electric arc at the individual welding points. The pulse regime ends after the second pressing of the trigger.

Certain technological processes have working regimes which are launched by pressing the trigger and then they continue until the next pressing of the trigger. The second pressing of the trigger is an instruction to end a given phase of the process. If the control switch of the activation light is connected with such a trigger—for example a trigger of the welding gun—at the end of the given phase, the activation light will receive inappropriate signal to light up, which will not be dangerous but which will decrease the comfort of the welder. In case of regimes that begin with the first pressing of the trigger and continue until the second pressing of the trigger, it is preferable if the activation light always lights up after the first pressing of the trigger and the control of the activation light always ignores the second pressing of the trigger. Such optional regime can be adjustable by the control mechanism of the activation light. It will be generally possible to adjust the counting sequence, i.e. which pressing is the first one and which is the second one.

It is possible to follow the same target, i.e. excluding the activation light at the second pressing of the switch in the aforementioned regime, while proceeding in such a way that the control of the activation light recognizes the ongoing technological process and decides that the pressing or holding of the switch during the ongoing phase of the technological phase is not an instruction to turn on the activation light. The ongoing technological process can be recognized by means of a second optical sensor connected to the control mechanism of the activation light.

There are also technological processes such as pulse welding where the pressing of the trigger, and thereby pressing of the switch, launches a phase of the process with the discontinuous light emission. In case the control of the activation light is connected with the control of the discontinuous process, the activation light will switch on and off discontinuously with each light emission. If the given device is completely independent and disconnected from the control of the activation light, it will be preferable if the control of the activation light recognizes the repeating cycles of the light emissions of the technological process. Such procedure can be part of the adaptation algorithm where the control mechanism will turn the activation light on before the calculated generation of the light emission on the basis of the regularly repeated appearance and disappearance of the light emission (without pressing the switch).

Apart for the issuance of the instruction to darken before the light emission generation, embodiments comprise the activation light to which the existing optical sensor of the protective equipment reacts. Pursuant to the state of the art, a cable transfer or radio-frequency channel could be used for the control of, say, a welding helmet but this would require a new helmet design. Such helmet would be compatible only with devices from the same producer and it would not be possible to use the solution on the existing helmets. It is the creation of the activation light according to this description that solves all these problems in a simple way. By means of the activation light, we produce a one-direction communication channel with the optical sensor on the protective equipment, while no modifications or complementary fittings of the protective equipment are needed. An existing optical sensor acts as a receiver in this one-direction communication channel. It suffices if the activation light is placed within the reach of the optical sensor of the protective equipment and this activation light will control all types of the protective equipment irrespective of their producer, since they all react to the light.

The activation light does not have problems with an interference in case it is placed nearby other workplaces with the activation light. It is simply true that if the activation light penetrates a neighboring workplace, then the dangerous light emission of the technological process penetrates it as well and it is necessary to better separate these workplaces, otherwise the protective equipment will darken following the instruction from the neighboring workplace. It is therefore not necessary to code or modulate the signal from the activation light in any way.

The abovementioned deficiencies in the prior state of the art are significantly remedied by the system for accelerated reaction of darkening of the optical device in personal protective equipment for sight protection. This system includes an optical sensor and an aperture with an optical device with adjustable permeability for the purposes of limitation of the penetration of the radiation from the light emission to the eyes. The optical sensor for detection of the light emission is placed within the protective equipment and it is connected to the control of the optical device. Embodiments include an activation light emitting a radiation that is detected by the optical sensor. The activation light has a switch intended for interface with the trigger of the technological device, whereby the activation light is placed within the reach of the optical sensor.

The activation light emits a radiation that falls within the sensitivity spectrum of the optical sensor in the protective equipment. Naturally, it should not be a dangerous ultraviolet radiation that personnel should be protected from. The activation light will usually consist of at least one infrared LED diode. Optical sensors are sensitive to the infrared light and even a low input power of the LED diode is sufficient to activate the optical sensor. A desired effect can be achieved through a construction and power supply of the LED diode which is used, for example, in the remote controls; power of the LED diode ranging from 0.1 to 2 W is sufficient. Such diodes are considered safe and harmless for human health. Use of the activation light—for example in the form of the infrared LED diode—kind of emulates or misleads the detection of the light emission of the technological process. After the activation light is turned on, the optical sensor evaluates the situation as if the light emission already occurred and it issues an instruction to darken the optical device. In reality, the light emission caused by the technological process, i.e. the light emission with dangerous radiation elements, occurs only after the lighting up of the activation light.

The aforementioned main features allow experts to use various realization options with particular technical means. In exemplary embodiments, the activation light can be placed at various places on the workplace within the reach of the optical sensor of the protective equipment. During the welding with welding torch—so-called welding gun—which has a trigger, it turned out to be adequate to place the switch of the activation light on the trigger of the welding gun or integrate it into the trigger, and place the activation light directly on the gun, for example at the mouth of the gun. In fact, the welder always holds the gun in such a way to see it during the work and the place of the light emission is located in the proximity of the gun. It results therefrom that the protective equipment—mainly a welding helmet—is with its optical sensor oriented in such a way that a welding gun is always in the field of view of the sensor.

Even in case the workplace is automated or robotized, the activation light is placed on the welding torch since the light emission will take place in its vicinity. In exemplary embodiments, an activation light can be placed in the fixed place on the production line, or it is possible to use multiple commonly controlled activation lights. Thus, each worker who looks at a given workplace from the expected side has one of the activation lights in the field of view of the optical sensor of the personal protective equipment.

When the activation light is switched on, it can be connected to a stable power supply or to a frequentially intermittent power supply. Certain optical sensors have increased sensitivity to a certain frequency range and so, the system can include and adjusting element for changing the supply frequency of the activation light. In such case the activation light will not only have a particular emitted wavelength but also a particular emitting frequency. In case of the frequentially intermittent power supply, it is preferable if the frequency is within a range from 5 to 250 Hz. Power supply of the activation light, frequency generator, delay adjustment element and other electronic elements necessary for the control of the activation light can be in this description and in the claims jointly named as control electronics or control unit.

The wavelength of the LED diode is basically stable; if there is a need to emit the light with various wavelengths, then multiple different LED diodes can be used within a single activation light which can be turned on either selectively or simultaneously. It is demonstrably preferable to use a spectrum of the wavelength within a range from 700 to 1850 nm.

Proposed invention can be used for new design of welding technologies but it will be very advantageously applicable especially to the existing welding devices. The main advantage lies in the fact that it is not necessary to modify the protective equipment itself in any way. The system includes a switch of the activation light intended for cooperation with the common trigger of the welding gun. The switch can have a form of a micro-switch whereby the trigger of the welding gun is pressed. So, during the pressing of the trigger a switch is pressed too. In order to achieve a high versatility of the device with the activation light, the activation light can be integrated into a ring that can be fixed and attached through the mouth of the welding torch. The ring is attached to the body of the torch or to the body of the gun. The ring carries at least one source of the activation light, preferably an infrared LED diode. For the distribution of the light emission to other parts of the ring, it is advantageous to use an optical diffuser. It is also possible to use multiple LED diodes with different or identical light emitting characteristics, i.e. mainly with different or identical wavelength. In case of multiple LED diodes, they can be distributed around and within the ring in order to secure reliable functioning of the activation light at various positions of the welding torch or welding gun.

Preferably, the activation light can be covered by a replaceable transparent protective cover which is resistant to heat, mechanical stress and sparks which arise during the technological process, mainly during welding. Such cover will be designed as an easily replaceable consumable material which can be replaced after the depreciation by a new piece without tools. The cover protects the surface of the activation light that, for example in case of the LED light, can be produced from plastic. The protective cover of the activation light can be circle-shaped or U-shaped and it can be produced from polycarbonate or glass.

Activation light or control electronics of the activation light can have—besides the switch—a control circuit for setting its characteristics. It is possible to set a delayed switching on of the light after the pressing of the switch. Furthermore, it is possible to adjust the frequency of the power supply. Preferably, the duration of the lighting that is deactivated by the activation light is adjusted too. The activation light can also have an indication of the low battery or other service functions. In order to increase the longevity of the battery, the activation light can have a power supply setting.

The trigger switch of the welding gun is connected to the control electronics of the activation light. In case of the welding guns for MIG/MAG, TIG, the trigger switch is usually a micro-switch with high longevity switch cycles. It is preferable if a galvanic division is created—for example by means of relay or opt coupler—for the switch after the control electronics is connected to it. The use of one switch for the launch of the welding process and control of the activation light can also have an inverse hierarchy where the switch of the control electronics is used to launch the welding process. This would mean that in case of the faulty switch of the control electronics—for example in case of the flat battery of the activation light—the welding itself does not start either. This improves the sight protection since the welding will be possible only with a functioning system.

A switch on the welding gun can be produced with a two-stroke mechanism, so the switching always takes place consecutively. This can be advantageously used in case a zero pre-blow time of the protective gas is set and the electric arc is ignited just after the pressing of the switch. With the two-stroke switch the first switch circuit controls the control electronics of the activation light and the second switch circuit starts the welding process itself. Thanks to this, there is a sufficient pre-ignition time even in case of a low or a zero pre-blow of the protective gas.

It will be also advantageous if the activation light can be turned on for the testing purposes even without launching the technological process. Such regime serves for a simple testing whether the given protective equipment reacts correctly to the activation light. In case the switch of the activation light itself is connected to the trigger of the welding gun, the trigger—and thereby the switch of the activation light—only needs to be pressed while the technological device is turned off (for example, while the welding machine or welding source is turned off). In case the switch of the activation light is incorporated in the technological device or the switch has a software form, the independent hardware or software testing switch for initiation of the activation light can be produced in a similar way.

The activation light together with the control electronics can be placed in the common body, on the common PCB board, which will be advantageous especially in case of the design intended to complement the existing welding guns which can be complemented without further modifying the welding gun itself. The design for an independent addition to the existing welding guns will be compact. In case of designing a new welding gun or in case of a hardware modification of the welding gun, it will be preferable to separate the control electronics and the activation light. This will ensure a better mechanical, radiation, electromagnetic and thermal protection of the control electronics which can be placed in the body of the welding gun, for example in the handle of the welding gun. The activation light requires only a small opening that can be created in the dividing plane of the molding of the gun. This will simplify the given modification of the injection mold.

Activation light placed in the welding gun can be located on the surface of its outer body or inside the body and the light flow of the activation light will be led to the surface of the welding gun by means of the optical conductor, which will improve the protection of the activation light. In this respect, there are multiple versions and combinations with varying number of sources of the activation light and with various designs of the conduction of the optical signal to the surface of the welding gun.

The placement of the control electronics inside the body of the welding gun offers good spatial possibilities of casing and it also offers sufficient space for the power source, for example an accumulator or a removable battery that can be accessible through the opening shaft. In order to achieve even larger building space without increasing the weight of the welding gun held by the welder, the control electronics can be placed outside of the welding gun, for example in the connecting terminal through which the hose with the protective gas and a cable with the welding current are connected to the welding machine. It can be for example a euro-connector which is used in its standardized design by multiple producers of the welding machines and welding sources. Electric conductors are then coming out of the control electronics towards the welding gun where the activation light is placed. The location of the control electronics inside or nearby the connector allows to create sufficiently large casing of the control electronics. Thanks to this design, the control electronics can have a power supply from its own adapter from the electricity network; alternatively, the adapter can be used to recharge the accumulator. The control electronics placed nearby or inside the connecting terminal significantly removes the risks arising in case of the vicinity of the welding process.

Placement of the activation light within or directly on the welding gun successfully covers most welding situations and most welding positions. Welder usually sees the welding gun in order to be able to move it alongside the weld. However, there are situations where the welder works in an environment in which the optical sensor of the protective equipment is covered (for example during welding of the metal frames). In such case the darkening of the protective equipment (helmet) may not take place at all because even if the welder properly sees the electric arc, the optical sensor is covered by the environment (for example a flat piece of metal right in front of the helmet across the field of view of the optical sensor) and the optical information causing the darkening of the protective equipment does not reach it.

This is a dangerous phenomenon because not only the delay of the darkening of the protective equipment, which is eliminated pursuant exemplary embodiments, will not take place, but there will be no darkening even during the light emission. Here the proposed exemplary embodiment offers an advantage of the independent transfer of the information concerning the light emission. One of the sources of the activation light can be produced as an external source, connected to the control electronics by means of a flexible cable and attached on the sleeve, glove or another appropriate place. In order to attach the external source of the activation light, it is possible to use a Velcro fastener, a clip or another appropriate mechanical means. Alternatively, for this purpose, it is possible to design a clothing or a glove with, say, a small transparent pocket sewn to it which also constitutes a protective cover. Externally attachable activation light can be the only one or it can be only an additional activation light within a system consisting of multiple sources of activation light. The external source of the activation light can be connected through a cable to the connector (for example a jack plug) placed on the surface of the welding gun. Depending on the setting, the connection can deactivate the stable activation light or both sources can be active simultaneously. The external source of the activation light can be attached to the body of the welder closer to the optical sensor or directly on the protective equipment, for example on the helmet.

The described principle of the activation of the optical device with the changing permeability can be also used for increasing the sensitivity of the protective equipment with lower quality and sensitivity, that does not guarantee a proper sight protection and does not recognize the light emission to a reliable extent, or only at a higher intensity. In order to improve the transfer of the optical information from the activation light, it is possible to use a signal repetition component which detects on its input when the activation light is turned on and on its output, it then turns on its own activation light. This component works as its spatial diffuser, extender or amplifier. It can be used in a situation when the optical sensor on the protective equipment is shielded or in a situation when the optical sensor is not sensitive enough. The signal repetition component can be attached in the close proximity of the optical sensor; i.e. for example directly on the welding helmet. The activation light of the signal repetition component will be placed in the proximity of the optical sensor.

The power supply of the control electronics can be ensured with one-off removable battery; the energy demands of the system are low. It is also possible to use a rechargeable accumulator that is replaceable or that can be charged with an adapter or from the solar cell as the welding helmet. On the basis of another adequate solution, the accumulator is charged by the induction of the flowing current in the welding cable. The proximity of the welding cable and hose with the flowing protective gas can be used also for charging with dynamo with a little propeller, which uses the energy of the flowing protective gas. The last but not least possibility is the supply from the stable electric source through an appropriate adapter. Such connection is advantageous mainly when the control electronics of the activation light is placed outside the welding gun, for example in the connector of the cable and the hose.

An important advantage of the proposed solution is its universal use in relation with any protective equipment which has an optical sensor for detecting the light emission of the technological process. The solution can be used with the existing welding helmets, masks, shields or goggles. Moreover, the technological process can be manual, automated or combined. Usually it will be arc or laser welding, cutting, plasma cutting, etc. The solution is advantageous especially when used during the arc welding with protective gas. The method and system do not require any modification or completion of the protective equipment. With this solution, even protective equipment with slow reaction, i.e. cheap protective equipment, can achieve very short, basically zero or negative reaction time in relation to the point in time when the light emission of the technological process appears. This will allow to lower the overall costs for the protection of sight and to improve health of the welders.

BRIEF DESCRIPTION OF DRAWINGS

Embodiments are explained in FIGS. 2 to 18. The used scales and ratios between the individual elements of the system, the shape of the activation light as well as the displayed temporal ratios are not binding, they are informative or they have been directly adjusted in order to increase the clarity.

Subsequently.

EXAMPLES OF REALIZATION

Example 1

As depicted in this example in FIGS. 2, 3, 4, 5, 10 and 11, the system is used in a common workshop without system integration. The welding apparatus for the MIG/MAG welding by the melting electrode in protective atmosphere has a welding gun 5 with the trigger which starts the technological process—the inflow of the gas, the movement of the wire and the electric arc. The welder has an auto-darkening helmet which is produced by a different producer than the welding device. During the welding, the welding helmet reacts to the detected light emission of the welding. The welding helmet in this example has a reaction time of the darkening at the level of 0.15 ms. During this period, the sight of the welder is exposed to the effects of the dangerous radiation.

The set in this example is supplied by the activation light 3. It is part of the small ring with an inner diameter larger than the diameter of the torch on the welding gun 5. The ring has removable inner circles the gradual removal or addition of which can set the desired inner diameter of the ring. There are two infrared LED diodes placed on the opposite sides inside the ring. Both are covered by the optical diffuser 8 which distributes the emitted light to the environment.

Both infrared LED diodes have wavelength 850 nm, approximate angular spread of 140° and they have a power supply from common source which has a frequency excitation on its output. The value of frequency on the frequency generator 6 is adjustable by means of a small rotary potentiometer ranging from 5 to 250 Hz. Similarly, it is also possible to adjust the duration of the delay of the beginning of the activation light from the moment the switch 4 is triggered. This period can be set from 0 to 1 second with help of adjusting element 7 of delay. The third adjusting element serves to set the duration of the activation lighting. In this example, the duration can be set from 1 to 3 seconds. The fourth adjusting element changes the power supply of the infrared LED diodes; in common conditions the activation is possible through the power supply of one 250 mW LED diode. The harmlessness of the activation light 3 for the unprotected eyes of the surrounding personnel is proved by the fact that the used LED diode is used in remote controllers of the home electronics. The use of the infrared remote controller is not considered a risk even in the situation where the invisible radiation is directed straight to the human eyes.

The switch 4 of the activation light 3 has in this example form of a flat switch circuit which is glued to the controlling edge of the trigger. The pressing of the trigger causes, firstly, the pressing of the switch 4 and then also turning on of the trigger of the welding apparatus.

After the pressing of the trigger of the welding gun 5, the welding apparatus opens a valve with the protective gas. Approximately 0.5 s after the opening of the valve the electric arc is turned on which starts the technological process. Simultaneously with the pressing of the trigger, the switch 4 of the activation light 3 has been pressed. The control circuit delays the turning on of the activation light 3 by approximately 0.4 s since the pressing of the switch 4. At that moment, the activation light 3 is on and the optical sensor 1 on the welding helmet reacts in such a way that it issues an instruction to darken the optical device 2. This instruction enters the optical device 2 approximately 0.1 s before the ignition of the electric arc itself. After 0.5 s when the light emission of the welding appears, the welding helmet is already darkened. Thus, the negative time of darkening of the welding helmet was basically reached at approximately 0.1 s.

Example 2

An automatic welding line in the car body workshop have multiple activation lights 3 distributed on fixed spots. The control welding system issues an instruction to initiate the activation light 3 approx. 0.1 s before the instruction to ignite the electric arc in a given section of the line. Workers who supervise the process watch the line through the welding helmet equipped with an auto-darkening optical device 2. This device reacts to the instruction received from the optical sensor 1 which detects the activation light first and then the light emission of the technological process itself.

Example 3

The system from this example is used in the laser cutting machine. The switch 4 has a software form. Before bringing the laser beam to the place of cutting, the instruction is issued by the central control system to light up the activation lights 3 placed on the working arm as well as at the edges of the table. One activation light 3 can be controlled directly, other activation lights can be integrated into independent signal repetition components 11.

Example 4

Figure 6:
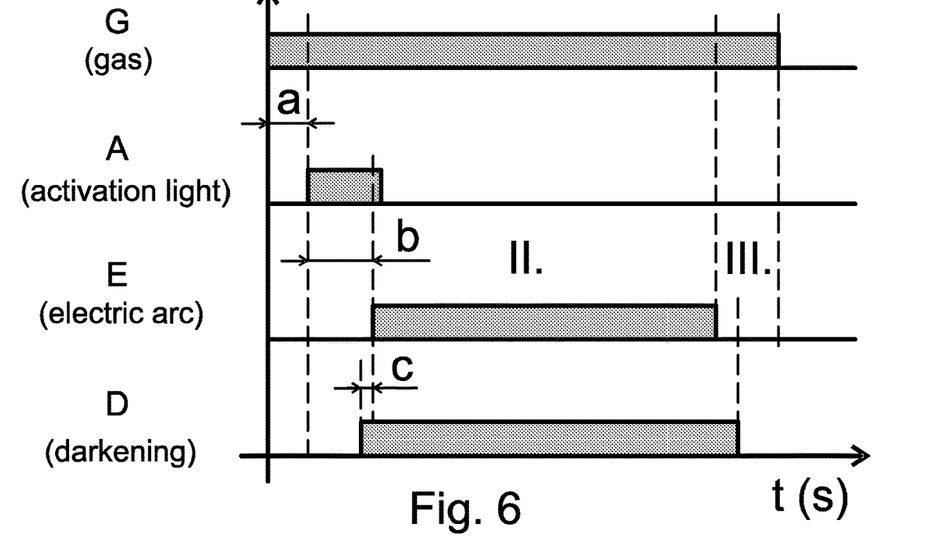
FIG. 6 is a time graph with the course of the welding and darkening of the protective equipment with the turning off of the activation light after detecting the light emission. The duration of the activation lighting is shorter than in the case of FIG. 2 where the activation light is on for a set period of time. The time a is an intentional delay of the turning on of the activation light with regard to the instruction to start the technological process. The time b is an advance time of the activation light before the light emission. The time c is an advance time of the darkening before the generation of the light emission.
Figure 12:
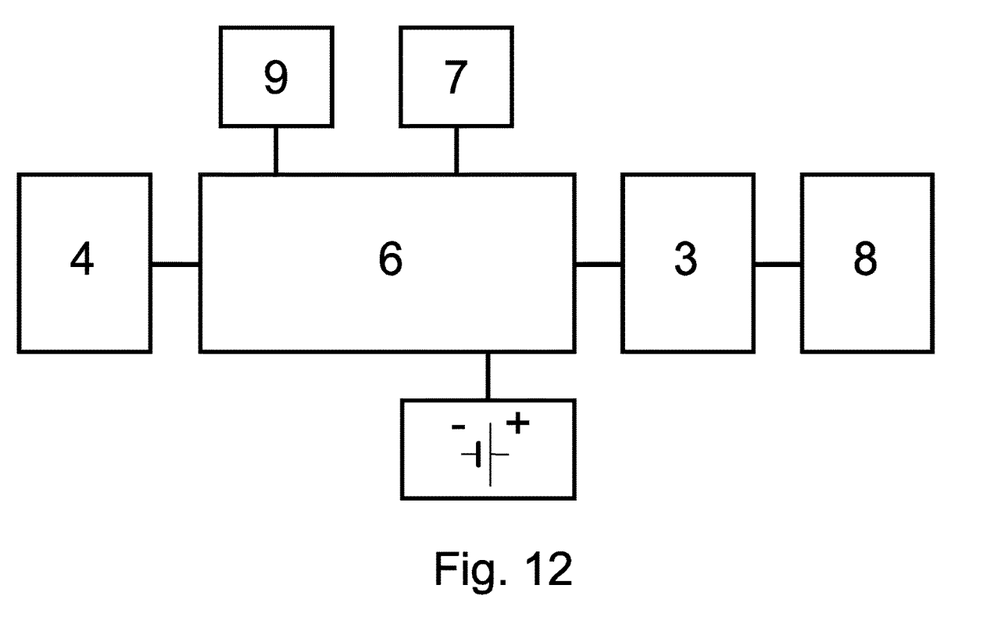
FIG. 12 is a block diagram of the control mechanism with the turning off of the activation light according to the instruction from the second optical sensor.

The activation light 3 displayed in FIGS. 6 and 12 has its own control mechanism for turning off the light. This function is based on the cooperation with the second optical sensor 9 which is placed in this example in the ring on the welding gun 5. The control of the activation light 3 receives an information that the second optical sensor 9 recorded a light emission of the technological process. This information means that the activation light is no longer needed and on the basis of this information the activation light 3 is turned off.

Since the second optical sensor 9 in the protective equipment can be faster than the optical sensor 1 of an unknown producer, the instruction to turn off the activation light 3 can be intentionally delayed by, say, 3 ms, which is a duration during which even a common or inferior protective equipment reacts to a light emission.

Example 5

Figure 7:
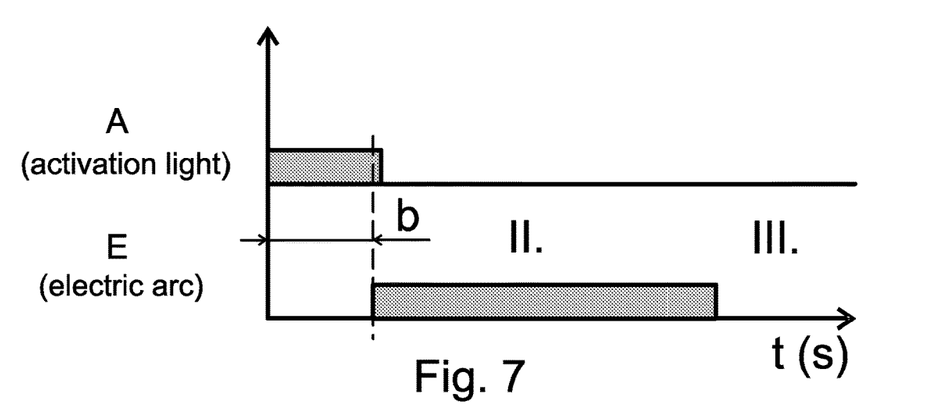
FIGS. 7 and 8 show the steps of adaptation of the control of the activation light. In the first step, according to FIG. 7 the activation light turns on right after the instruction to initiate the technological process. In the x-th step—for example already in the second step of the adaptation according to FIG. 8—the control has set the delay "a" which can be shortened even further in the next step. The activation lighting is depicted with the same duration in FIGS. 7 and 8 in order to increase clarity but this adaptation can be combined with the turning off of the activation light as depicted in FIG. 6.
Figure 8:
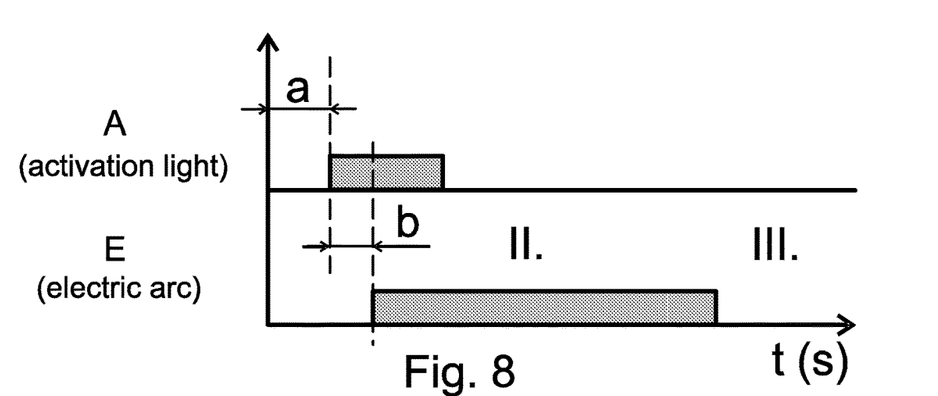

The control of the activation light 3 involves an adaptation algorithm that measures a time lapse between the instruction to initiate a technological process and the appearance of a light emission. According to the measured time period displayed in FIGS. 7 and 8, the delay of lighting up the activation light 3 is in various iterative steps gradually increased until the moment where the advance time of lighting up the activation light 3 with regard to the light emission reaches 0.1 s. This delay is then respected in the following strokes whereby it is continually measured whether there is sufficient advance time of lighting up the activation light 3 with regard to the light emission.

Example 6

Figure 13:
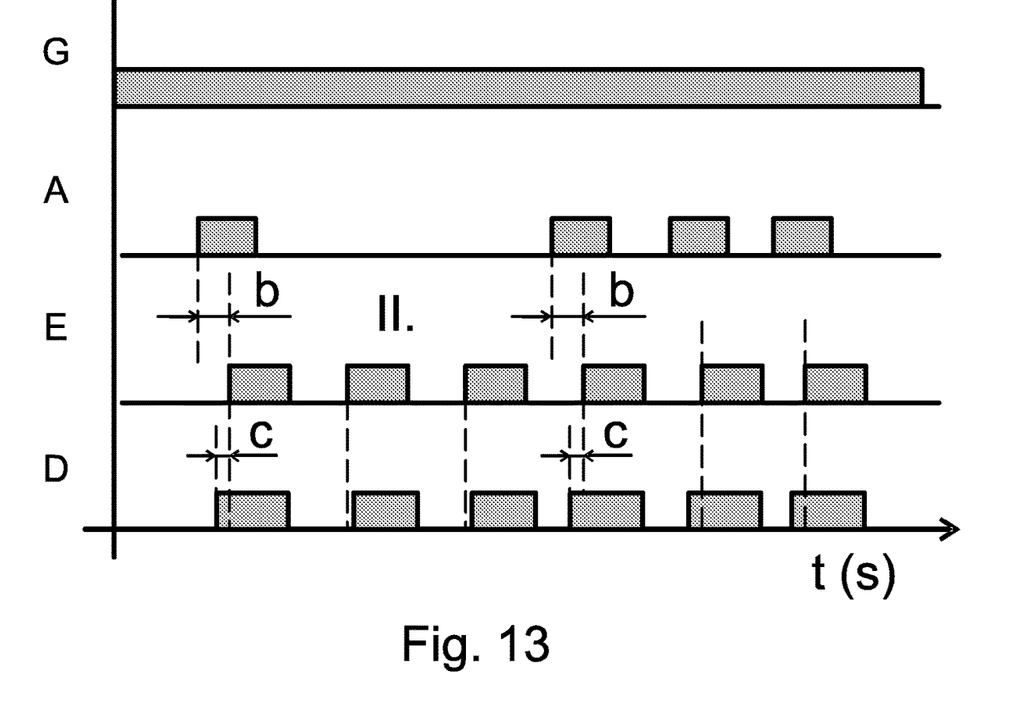
FIG. 13 depicts an adaptation of the control of the activation light during the technological process in which a series of cycles takes place after the first pressing of the trigger. The activation light is turned on after the first pressing of the trigger and then for two cycles the protective equipment is darkened only on the basis of the detection of the light emission itself.

The activation light 3 is turned on after the first pressing of the trigger, then during two cycles the protective equipment is darkened only on the basis of the detection of the light emission itself because the cycles were not accompanied by the pressing of the switch 4. During three cycles the control of the activation light 3 adapts to the detected course of the light emission and before the expected fourth and each following light emission, the control mechanism lights up the activation light 3. Consequently, the second and the third darkening of the protective equipment is delayed according to the reaction time of the given protective equipment; the next darkening is realized with the advance time.

Example 7

Figure 14:
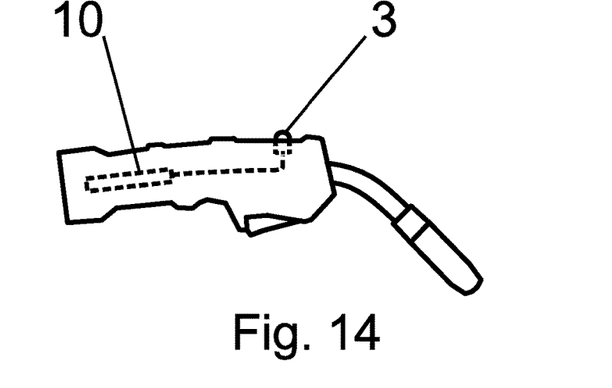
FIG. 14 depicts the placement of the control electronics inside the body of the welding gun.

The activation light 3 displayed in FIG. 14 is cased in the plastic body of the welding gun 5. On the surface of the welding gun 5 there is an opening with a protruding removable cover of the LED diode of the activation light 3. The cover is produced from the transparent plastic and in case of damage it can be removed by rotation and changed.

The control electronics 10 is placed in the handle of the welding gun 5, which also contains an opening shaft where a battery or a rechargeable accumulator can be inserted.

Example 8

Figure 15:
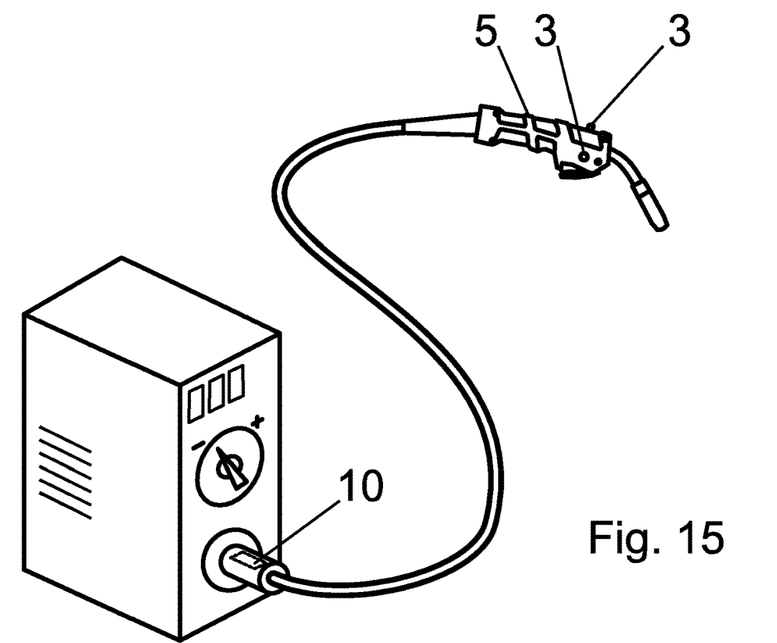
FIG. 15 depicts the placement of the control electronics in the euro-connector of the hose and the cable.

As shown in FIG. 15, the activation light 3 with three sources in form of the LED diodes is placed in the plastic body of the welding gun 5 in the similar way as in the previous example. The control electronics 10 is placed in the connector of the hose and the electric cable—in this example it is a standardized euro-connector. The activation light 3 receives a power supply through a thin cable connected to the hose with protective gas.

Example 9

Figure 16:
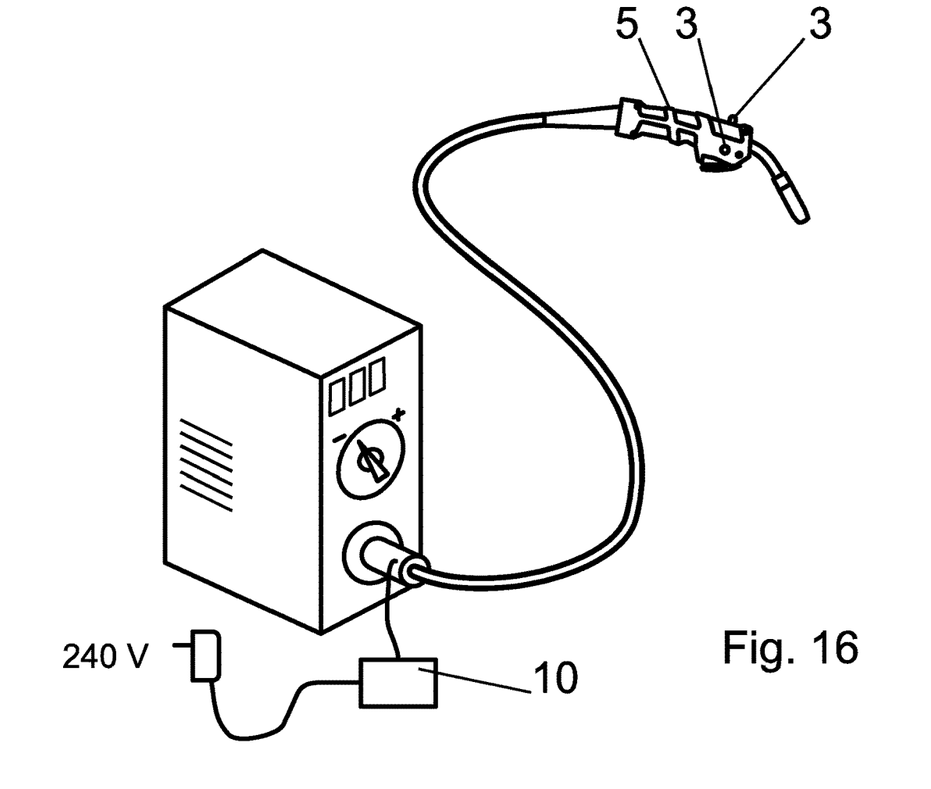
FIG. 16 depicts the independent placement of the control electronics supplied by power from the AC/DC electric adapter.

The control electronics 10 is in an independent box which is close to the welding machine. The connecting cable connecting the control electronics 10 with the activation light 3 is attached to the hose with protective gas. The power supply of the control electronics 10 and the activation light 3 is provided by an AC/DC adapter, in this example with a micro USB terminal, i.e. a corresponding connector on the body of the control electronics 10. The use of the 5V USB power supply adapter simplifies the construction of the system.

Example 10

Figure 17:
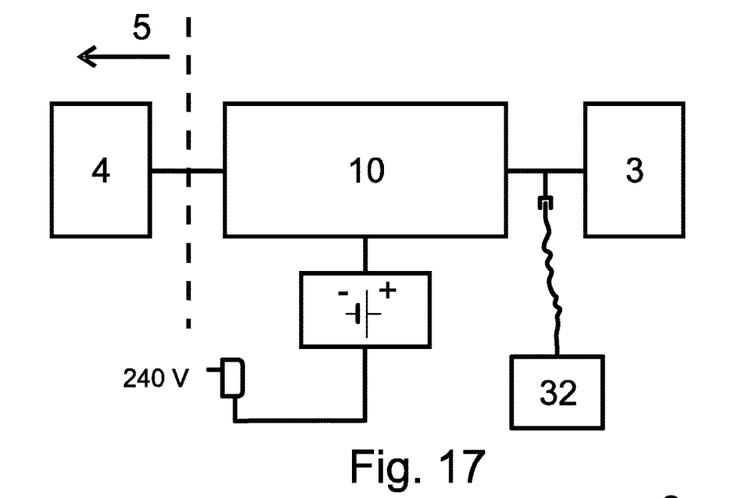
FIG. 17 is a schematic connection of the external activation light, and it is also shown that the switch of the control electronics is the trigger of the welding gun.

As shown in this example in FIG. 17, the trigger of the welding gun 5 itself is used as a switch 4. On the surface of the welding gun 5 there is a jack connector allowing the connection of the external activation light 32. This has a form of the LED diode in the casing with a mechanical clip that can be attached to a glove or a sleeve of the protective clothing of the welder. In this example, the external activation light 32 is turned on together with the activation light 3 on the welding gun 5.

Example 11

Figure 18:
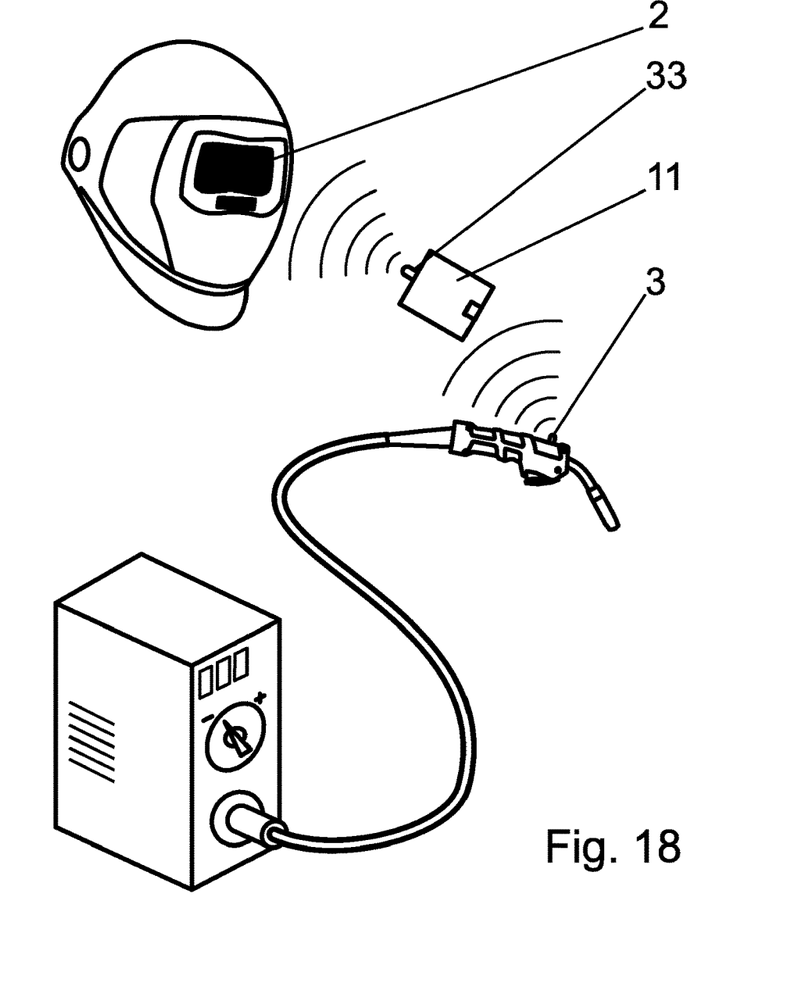
FIG. 18 depicts a signal repetition component which carries a signal from the activation light to the proximity of the optical sensor on the welding helmet.

As depicted in the example in FIG. 18, the system has an independent signal repetition component 11. It has an outer form of a small box with its own source of the electric energy. The signal repetition component 11 has a receiver of the optical signal and a transmitter in form of the activation light 33 for signal repetition. After receiving the light from the activation light 3, the activation light 33 for signal repetition, which can be attached closer to the optical sensor 1 of the welding helmet, is turned on. Signal repetition component 11 can have an adhesive layer, so that the activation light 33 for signal repetition could be directly glued within the field of view of the optical sensor 1 of the welding helmet.

LIST OF RELATED SYMBOLS

1—optical sensor
2—optical device with changeable permeability
3—activation light
32—external activation light
33—activation light for signal repetition
4—switch
5—welding gun
6—frequency generator
7—adjusting element of delay
8—optical diffuser
9—second optical sensor
10—control electronics
11—signal repetition component
MIG—Metal Inert Gas
MAG—Metal Active Gas
TIG, WIG—tungsten (wolfram) inert gas welding
PCB—printed circuit board
240 V—electricity network with alternating voltage
ADF—automatic darkening filters

The invention claimed is:

1. A system for an accelerated reaction of a darkening of an optical element (2) for protection from a luminous manifestation of a technological device configured to perform arc or laser welding or cutting or plasma cutting, the system comprising:
a protective device, the protective device being a welding helmet or a welding mask or a welding shield or welding goggles, and
a technological device configured to perform arc or laser welding or cutting or plasma cutting;
wherein the protective device comprises an optical sensor (1) for a detection of the luminous manifestation,
wherein the protective device comprises an optical element (2) with an adjustable permeability for a limitation of a permeation of a radiation from the luminous manifestation to a sight,
wherein the optical sensor (1) is connected with a control of the optical element (2), and
wherein the technological device comprises an activation light (3) configured to emit radiation which is detected by the optical sensor (1), whereby the activation light (3) is placed within a field of a vision of the optical sensor (1),
the technological device comprises a trigger which can be pressed to start the arc or laser welding or cutting or plasma cutting;
wherein
the technological device comprises a switch (4) connected with the trigger such that during the pressing of the trigger the switch (4) is pressed too,
the activation light (3) is connected to the switch (4), and
wherein controlling electronics (10) of the activation light (3) are part of a body of a welding gun (5) or it is a part of a connecting end of a tube and electric cables which connect the welding gun (5) with a welding source, whereby the controlling electronics (10) are connected with the activation light (3) by means of electric conductors which are at least in part of their length connected to a bunch of the tube and the electric cables.

2. The system according to claim 1 wherein the activation light (3) has at least one infrared LED diode.

3. The system according to claim 1 wherein the system includes multiple LED diodes.

4. The system according to claim 1 wherein the activation light (3) is part of a body which is adjusted for a connection to a welding gun (5), wherein the body carries an adjusting element, a power supply and the switch (4).

5. The system according to claim 4 wherein the body is ring-shaped.

6. The system according to claim 1, wherein the activation light (3) has an optical diffuser (8).

7. The system according to claim 1 wherein the technological device includes a generator (6) of a frequency of a power supply of the activation light (3), wherein the generator (6) is adjustable.

8. The system according to claim 1 wherein the technological device includes an adjustable element (7) for adjusting a delay of the activation light (3) relative to the switching of the switch (4).

9. The system according to claim 1 wherein the technological device includes an adjustment element for adjusting a period of shining of the activation light (3).

10. The system according to claim 1 wherein the technological device includes a second optical sensor (9) for the detection of the luminous manifestation, which is connected with a control of the activation light (3).

11. The system according to claim 1 wherein the switch (4) is a switch of a welding gun (5).

12. The system according to claim 1 wherein the activation light (3) is a part of a body of a welding gun (5).

13. The system according to claim 1 wherein the system has at least one external activation light (32) which is connected with the controlling electronics (10) by a flexible cable.

14. The system according to claim 1 wherein a power supply of the controlling electronics (10) and the activation light (3) has a battery or a rechargeable battery and/or a solar cell and/or an induction charger positioned adjacent to welding cables and/or an AC/DC adapter.

15. A method for an accelerated reaction of a darkening of an optical element (2) for protection from a luminous manifestation of a technological device configured to perform arc or laser welding or cutting or plasma cutting, by using the system of claim 1, the method comprising the steps of pressing the trigger of said technological device, the pressing of the trigger causing a pressing of the switch (4) causing the turning on of the activation light (3)

the activation light (3) causing activation of the optical sensor (1) before the optical sensor (1) detects the luminous manifestation.

16. The method according to claim 15 wherein the activation light (3) shines at least until a point where the optical sensor (1) detects the luminous manifestation.

17. The method according to claim 15 wherein the activation light (3) shines for a preset time since it lights up.

18. The method according to claim 15 wherein the activation light (3) goes off after its control receives information about the detection of the luminous manifestation.

19. The method according to claim 15 wherein the activation light (3) lights up 0.05 to 0.5 second before the creation of the luminous manifestation.

20. The method according to claim 15 wherein the activation light (3) emits the radiation with a wavelength between 700 and 1850 nm.

21. The method according to claim 15 wherein the activation light (3) shines with the frequency ranging from 5 to 250 Hz.

22. A system for an accelerated reaction of a darkening of an optical element (2) for protection from a luminous manifestation of a technological device configured to perform arc or laser welding or cutting or plasma cutting, the system comprising:

a protective device, the protective device being a welding helmet or a welding mask or a welding shield or welding goggles, and a technological device configured to perform arc or laser welding or cutting or plasma cutting;

wherein the protective device comprises an optical sensor (1) for a detection of the luminous manifestation, wherein the protective device comprises an optical element (2) with an adjustable permeability for a limitation of a permeation of a radiation from the luminous manifestation to a sight, wherein the optical sensor (1) is connected with a control of the optical element (2), and wherein the technological device comprises an activation light (3) configured to emit radiation which is detected by the optical sensor (1), whereby the activation light (3) is placed within a field of a vision of the optical sensor (1), the technological device comprises a trigger which can be pressed to start the arc or laser welding or cutting or plasma cutting;

wherein the technological device comprises a switch (4) connected with the trigger such that during the pressing of the trigger the switch (4) is pressed too, the activation light (3) is connected to the switch (4), and the system further comprising a signal repeating element (11) which has a receiver of an optical signal of the activation light (3) and it has a transmitter in form of an activation light (33) to repeat the optical signal, whereby the signal repeating element (11) is adjusted for an independent placement in a vicinity of the optical sensor (1).

* * * * *